(12) United States Patent
Duke

(10) Patent No.: US 7,981,092 B2
(45) Date of Patent: Jul. 19, 2011

(54) VIBRATORY TROCAR

(75) Inventor: Daniel H. Duke, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 525 days.

(21) Appl. No.: 12/116,998

(22) Filed: May 8, 2008

(65) Prior Publication Data

US 2009/0281478 A1    Nov. 12, 2009

(51) Int. Cl.
*A61M 5/00* (2006.01)
(52) U.S. Cl. ........................................ 604/264
(58) Field of Classification Search ............ 606/167, 606/171, 79, 184, 169, 174; 604/164.1, 264, 604/272; 600/437, 464, 471, 562–572
See application file for complete search history.

(56) References Cited

U.S. PATENT DOCUMENTS

| 3,315,663 | A | 4/1967 | Goldfarb |
| 3,900,022 | A | 8/1975 | Widran |
| 3,903,877 | A | 9/1975 | Terada et al. |
| 3,924,608 | A | 12/1975 | Mitsui et al. |
| 3,980,078 | A | 9/1976 | Tominaga et al. |
| 3,981,276 | A | 9/1976 | Ernest |
| 4,204,563 | A | 5/1980 | Pyle |
| 4,279,246 | A | 7/1981 | Chikama et al. |
| 4,687,033 | A | 8/1987 | Furrow et al. |
| 4,690,140 | A | 9/1987 | Mecca |
| 4,722,000 | A | 1/1988 | Chatenever |
| 4,836,187 | A | 6/1989 | Iwakoshi et al. |
| 4,874,364 | A | 10/1989 | Morris et al. |
| 4,877,016 | A | 10/1989 | Kantor et al. |
| 4,919,305 | A | 4/1990 | Podgers |
| 4,943,280 | A | 7/1990 | Lander |
| 5,084,057 | A | 1/1992 | Green et al. |
| 5,104,383 | A | 4/1992 | Shichman |
| 5,112,308 | A | 5/1992 | Olsen et al. |
| 5,127,909 | A | 7/1992 | Shichman |
| 5,167,220 | A | 12/1992 | Brown |
| 5,180,373 | A | 1/1993 | Green et al. |
| 5,191,878 | A | 3/1993 | Iida et al. |
| 5,197,955 | A | 3/1993 | Stephens et al. |
| 5,201,714 | A | 4/1993 | Gentelia et al. |

(Continued)

FOREIGN PATENT DOCUMENTS

CA    2060930-AA    10/1992

(Continued)

OTHER PUBLICATIONS

Extended European Search Report (EP 09 25 1267) dated Aug. 6, 2009.

(Continued)

*Primary Examiner* — Kevin T Truong
(74) *Attorney, Agent, or Firm* — Nutter McClennen & Fish LLP

(57) ABSTRACT

Devices and methods are provided for removing fluid from a trocar or from surgical instruments passed therethrough, and for preventing such fluid from accumulating. For example, an exemplary method for removing fluid from a trocar can include positioning a trocar to extend into a body cavity and vibrating the trocar to prevent fluid in the trocar from being deposited on surgical instruments passed therethrough. In one embodiment, the trocar can be selectively vibrated by activating a foot pedal or remote control, or according to an output of a sensor.

20 Claims, 8 Drawing Sheets

U.S. PATENT DOCUMENTS

| | | |
|---|---|---|
| 5,207,213 A | 5/1993 | Auhll et al. |
| 5,209,737 A | 5/1993 | Ritchart et al. |
| 5,226,891 A | 7/1993 | Bushatz et al. |
| 5,237,984 A | 8/1993 | Williams, III et al. |
| 5,279,542 A | 1/1994 | Wilk |
| 5,312,351 A | 5/1994 | Gerrone |
| 5,312,363 A | 5/1994 | Ryan et al. |
| 5,312,397 A | 5/1994 | Cosmescu |
| 5,313,934 A | 5/1994 | Wiita et al. |
| 5,320,608 A | 6/1994 | Gerrone |
| 5,320,610 A | 6/1994 | Yoon |
| 5,326,013 A | 7/1994 | Green et al. |
| 5,330,437 A | 7/1994 | Durman |
| 5,334,164 A | 8/1994 | Guy et al. |
| 5,337,730 A | 8/1994 | Maguire |
| 5,339,800 A | 8/1994 | Wiita et al. |
| 5,342,315 A | 8/1994 | Rowe et al. |
| 5,347,988 A | 9/1994 | Hori |
| 5,354,302 A | 10/1994 | Ko |
| 5,364,002 A | 11/1994 | Green et al. |
| 5,369,525 A | 11/1994 | Bala et al. |
| 5,382,297 A | 1/1995 | Valentine et al. |
| 5,389,081 A | 2/1995 | Castro |
| 5,391,154 A | 2/1995 | Young |
| 5,392,766 A | 2/1995 | Masterson et al. |
| 5,395,342 A | 3/1995 | Yoon |
| 5,400,767 A | 3/1995 | Murdoch et al. |
| 5,419,309 A | 5/1995 | Biehl |
| 5,441,513 A | 8/1995 | Roth |
| 5,443,452 A | 8/1995 | Hart et al. |
| 5,448,990 A | 9/1995 | De Faria-Correa et al. |
| 5,449,370 A * | 9/1995 | Vaitekunas .................. 606/169 |
| 5,458,633 A | 10/1995 | Bailey |
| 5,458,640 A | 10/1995 | Gerrone |
| 5,462,100 A | 10/1995 | Covert et al. |
| 5,464,008 A | 11/1995 | Kim |
| 5,476,475 A | 12/1995 | Gadberry |
| 5,486,154 A | 1/1996 | Kelleher |
| 5,492,304 A | 2/1996 | Smith et al. |
| 5,496,280 A | 3/1996 | Vandenbroek et al. |
| 5,496,345 A | 3/1996 | Kieturakis et al. |
| 5,496,411 A | 3/1996 | Candy et al. |
| 5,514,084 A | 5/1996 | Fisher |
| 5,514,153 A | 5/1996 | Bonutti |
| 5,518,026 A | 5/1996 | Benjey |
| 5,518,502 A | 5/1996 | Kaplan et al. |
| 5,533,496 A | 7/1996 | De Faria-Correa et al. |
| 5,535,759 A | 7/1996 | Wilk |
| 5,536,234 A | 7/1996 | Newman |
| 5,542,931 A | 8/1996 | Gravener et al. |
| 5,545,142 A | 8/1996 | Stephens et al. |
| 5,545,179 A | 8/1996 | Williamson, IV |
| 5,549,543 A | 8/1996 | Kim |
| 5,551,448 A | 9/1996 | Matula et al. |
| 5,554,151 A | 9/1996 | Hinchliffe |
| 5,568,828 A | 10/1996 | Harris |
| 5,569,183 A | 10/1996 | Kieturakis |
| 5,569,205 A | 10/1996 | Hart et al. |
| 5,575,756 A | 11/1996 | Karasawa et al. |
| 5,584,850 A | 12/1996 | Hart et al. |
| 5,590,697 A | 1/1997 | Benjey et al. |
| 5,603,702 A | 2/1997 | Smith et al. |
| 5,605,175 A | 2/1997 | Bergsma et al. |
| 5,628,732 A | 5/1997 | Antoon, Jr. et al. |
| 5,630,795 A | 5/1997 | Kuramoto et al. |
| 5,634,911 A | 6/1997 | Hermann et al. |
| 5,643,227 A | 7/1997 | Stevens |
| 5,643,301 A | 7/1997 | Mollenauer |
| 5,647,372 A | 7/1997 | Tovey et al. |
| 5,647,840 A | 7/1997 | D'Amelio et al. |
| 5,651,757 A | 7/1997 | Meckstroth |
| 5,658,273 A | 8/1997 | Long |
| 5,662,614 A | 9/1997 | Edoga |
| 5,685,823 A | 11/1997 | Ito et al. |
| 5,688,222 A | 11/1997 | Hluchy et al. |
| 5,709,664 A | 1/1998 | Vandenbroek et al. |
| 5,720,756 A | 2/1998 | Green et al. |
| 5,720,759 A | 2/1998 | Green et al. |
| 5,725,477 A | 3/1998 | Yasui et al. |
| 5,725,478 A | 3/1998 | Saad |
| 5,743,884 A | 4/1998 | Hasson et al. |
| 5,752,938 A | 5/1998 | Flatland et al. |
| 5,755,252 A | 5/1998 | Bergsma et al. |
| 5,755,732 A | 5/1998 | Green et al. |
| 5,782,859 A | 7/1998 | Nicholas et al. |
| 5,788,676 A | 8/1998 | Yoon |
| 5,792,044 A | 8/1998 | Foley et al. |
| 5,792,113 A | 8/1998 | Kramer et al. |
| 5,797,434 A | 8/1998 | Benjey et al. |
| 5,807,338 A | 9/1998 | Smith et al. |
| 5,814,026 A | 9/1998 | Yoon |
| 5,817,061 A | 10/1998 | Goodwin et al. |
| 5,848,992 A | 12/1998 | Hart et al. |
| 5,860,458 A | 1/1999 | Benjey et al. |
| 5,871,440 A | 2/1999 | Okada et al. |
| 5,882,345 A | 3/1999 | Yoon |
| 5,902,231 A | 5/1999 | Foley et al. |
| 5,902,264 A | 5/1999 | Toso et al. |
| 5,906,595 A | 5/1999 | Powell et al. |
| 5,954,635 A | 9/1999 | Foley et al. |
| 5,957,888 A | 9/1999 | Hinchliffe |
| 5,964,781 A | 10/1999 | Mollenauer et al. |
| 5,983,958 A | 11/1999 | Bergsma et al. |
| 5,989,224 A | 11/1999 | Exline et al. |
| 6,004,326 A | 12/1999 | Castro et al. |
| 6,007,487 A | 12/1999 | Foley et al. |
| 6,017,333 A | 1/2000 | Bailey |
| 6,062,276 A | 5/2000 | Benjey et al. |
| 6,063,050 A | 5/2000 | Manna et al. |
| 6,110,103 A | 8/2000 | Donofrio |
| 6,126,592 A | 10/2000 | Proch et al. |
| 6,152,871 A | 11/2000 | Foley et al. |
| 6,159,182 A | 12/2000 | Davis et al. |
| 6,162,170 A | 12/2000 | Foley et al. |
| 6,167,920 B1 | 1/2001 | Enge |
| 6,176,823 B1 | 1/2001 | Foley et al. |
| 6,176,825 B1 | 1/2001 | Chin et al. |
| 6,206,057 B1 | 3/2001 | Benjey et al. |
| 6,206,822 B1 | 3/2001 | Foley et al. |
| 6,216,661 B1 | 4/2001 | Pickens et al. |
| 6,217,509 B1 | 4/2001 | Foley et al. |
| 6,253,802 B1 | 7/2001 | Enge |
| 6,258,065 B1 | 7/2001 | Dennis et al. |
| 6,264,604 B1 | 7/2001 | Kieturakis et al. |
| 6,287,313 B1 | 9/2001 | Sasso |
| 6,354,992 B1 | 3/2002 | Kato |
| 6,371,909 B1 | 4/2002 | Hoeg et al. |
| 6,409,657 B1 | 6/2002 | Kawano |
| 6,423,266 B1 | 7/2002 | Choperena et al. |
| 6,425,535 B1 | 7/2002 | Akiba et al. |
| 6,425,859 B1 | 7/2002 | Foley et al. |
| 6,428,491 B1 | 8/2002 | Weiss |
| 6,443,190 B1 | 9/2002 | Enge |
| 6,447,446 B1 | 9/2002 | Smith et al. |
| 6,482,181 B1 | 11/2002 | Racenet et al. |
| 6,494,893 B2 | 12/2002 | Dubrul et al. |
| 6,497,687 B1 | 12/2002 | Blanco |
| 6,516,835 B2 | 2/2003 | Enge |
| 6,520,907 B1 | 2/2003 | Foley et al. |
| 6,534,002 B1 | 3/2003 | Lin et al. |
| 6,551,282 B1 | 4/2003 | Exline et al. |
| 6,562,046 B2 | 5/2003 | Sasso |
| 6,569,120 B1 | 5/2003 | Green et al. |
| 6,595,915 B2 | 7/2003 | Akiba et al. |
| 6,595,946 B1 | 7/2003 | Pasqualucci |
| 6,601,617 B2 | 8/2003 | Enge |
| 6,605,098 B2 | 8/2003 | Nobis et al. |
| 6,638,214 B2 | 10/2003 | Akiba et al. |
| 6,648,906 B2 | 11/2003 | Lasheras et al. |
| 6,679,833 B2 | 1/2004 | Smith et al. |
| 6,679,834 B2 | 1/2004 | Stahl et al. |
| 6,679,837 B2 | 1/2004 | Daikuzono |
| 6,685,665 B2 | 2/2004 | Booth et al. |
| 6,699,185 B2 | 3/2004 | Gminder et al. |
| 6,702,787 B2 | 3/2004 | Racenet et al. |
| 6,712,757 B2 | 3/2004 | Becker et al. |
| 6,726,663 B1 | 4/2004 | Dennis |

| | | |
|---|---|---|
| 6,755,782 B2 | 6/2004 | Ogawa et al. |
| 6,860,869 B2 | 3/2005 | Dennis |
| 6,860,892 B1 | 3/2005 | Tanaka et al. |
| 6,918,924 B2 | 7/2005 | Lasheras et al. |
| 6,923,759 B2 | 8/2005 | Kasahara et al. |
| 6,942,671 B1 | 9/2005 | Smith |
| 6,981,966 B2 | 1/2006 | Green et al. |
| 6,989,003 B2 | 1/2006 | Wing et al. |
| 7,008,416 B2 | 3/2006 | Sakaguchi et al. |
| 7,025,747 B2 | 4/2006 | Smith |
| 7,052,454 B2 | 5/2006 | Taylor |
| 7,056,303 B2 | 6/2006 | Dennis et al. |
| 7,056,321 B2 | 6/2006 | Pagliuca et al. |
| 7,077,803 B2 | 7/2006 | Kasahara et al. |
| 7,083,626 B2 | 8/2006 | Hart et al. |
| 7,104,657 B2 | 9/2006 | Sherwin et al. |
| 7,105,009 B2 | 9/2006 | Johnson et al. |
| 7,112,185 B2 | 9/2006 | Hart et al. |
| 7,163,525 B2 | 1/2007 | Franer |
| 7,169,130 B2 | 1/2007 | Exline et al. |
| 7,198,598 B2 | 4/2007 | Smith et al. |
| 7,207,347 B2 | 4/2007 | Olshanetsky et al. |
| 7,244,244 B2 | 7/2007 | Racenet et al. |
| 7,344,519 B2 | 3/2008 | Wing et al. |
| 7,473,243 B2 | 1/2009 | Dennis et al. |
| 7,563,268 B2 * | 7/2009 | Ishikawa ............ 606/167 |
| 7,591,802 B2 | 9/2009 | Johnson et al. |
| 2002/0022762 A1 | 2/2002 | Beane et al. |
| 2002/0065450 A1 | 5/2002 | Ogawa |
| 2002/0068923 A1 | 6/2002 | Caldwell et al. |
| 2002/0103420 A1 | 8/2002 | Coleman et al. |
| 2002/0107484 A1 | 8/2002 | Dennis et al. |
| 2002/0161387 A1 | 10/2002 | Blanco |
| 2003/0004529 A1 | 1/2003 | Tsonton et al. |
| 2003/0060770 A1 | 3/2003 | Wing et al. |
| 2003/0130674 A1 | 7/2003 | Kasahara et al. |
| 2003/0139756 A1 | 7/2003 | Brustad |
| 2003/0195472 A1 | 10/2003 | Green et al. |
| 2004/0034339 A1 | 2/2004 | Stoller et al. |
| 2004/0106942 A1 | 6/2004 | Taylor et al. |
| 2004/0167559 A1 | 8/2004 | Taylor et al. |
| 2004/0171990 A1 | 9/2004 | Dennis et al. |
| 2004/0220452 A1 | 11/2004 | Shalman |
| 2004/0230161 A1 | 11/2004 | Zeiner |
| 2004/0256004 A1 | 12/2004 | Kessell et al. |
| 2004/0260244 A1 | 12/2004 | Piechowicz et al. |
| 2005/0004512 A1 | 1/2005 | Campbell et al. |
| 2005/0033342 A1 | 2/2005 | Hart et al. |
| 2005/0043683 A1 | 2/2005 | Ravo |
| 2005/0059865 A1 | 3/2005 | Kahle et al. |
| 2005/0059934 A1 | 3/2005 | Wenchell et al. |
| 2005/0070850 A1 | 3/2005 | Albrecht |
| 2005/0070946 A1 | 3/2005 | Franer et al. |
| 2005/0070947 A1 | 3/2005 | Franer et al. |
| 2005/0077688 A1 | 4/2005 | Voegele et al. |
| 2005/0077689 A1 | 4/2005 | Hueil |
| 2005/0096605 A1 | 5/2005 | Green et al. |
| 2005/0131349 A1 | 6/2005 | Albrecht et al. |
| 2005/0203543 A1 | 9/2005 | Hilal et al. |
| 2005/0216028 A1 | 9/2005 | Hart et al. |
| 2005/0241647 A1 | 11/2005 | Nguyen et al. |
| 2005/0288622 A1 | 12/2005 | Albrecht et al. |
| 2006/0020165 A1 | 1/2006 | Adams |
| 2006/0047240 A1 | 3/2006 | Kumar et al. |
| 2006/0052666 A1 | 3/2006 | Kumar et al. |
| 2006/0068360 A1 | 3/2006 | Boulais |
| 2006/0069312 A1 | 3/2006 | O'Connor |
| 2006/0100485 A1 | 5/2006 | Arai et al. |
| 2006/0122556 A1 | 6/2006 | Kumar et al. |
| 2006/0122557 A1 | 6/2006 | Kumar et al. |
| 2006/0129098 A1 | 6/2006 | Hart et al. |
| 2006/0135972 A1 | 6/2006 | Zeiner |
| 2006/0135977 A1 | 6/2006 | Thompson et al. |
| 2006/0135978 A1 | 6/2006 | Franer |
| 2006/0149137 A1 | 7/2006 | Pingleton et al. |
| 2006/0199998 A1 | 9/2006 | Akui et al. |
| 2006/0211916 A1 | 9/2006 | Kasahara et al. |
| 2006/0224121 A1 | 10/2006 | Hart et al. |
| 2006/0224164 A1 | 10/2006 | Hart et al. |
| 2006/0229565 A1 | 10/2006 | Dennis et al. |
| 2006/0235455 A1 | 10/2006 | Oshida |
| 2006/0276688 A1 | 12/2006 | Surti |
| 2006/0293559 A1 | 12/2006 | Grice et al. |
| 2007/0005087 A1 | 1/2007 | Smith et al. |
| 2007/0021713 A1 | 1/2007 | Kumar et al. |
| 2007/0027453 A1 | 2/2007 | Hart et al. |
| 2007/0088275 A1 | 4/2007 | Stearns et al. |
| 2007/0088277 A1 | 4/2007 | McGinley et al. |
| 2007/0129719 A1 | 6/2007 | Kendale et al. |
| 2007/0142709 A1 | 6/2007 | Martone et al. |
| 2007/0149931 A1 | 6/2007 | Cannon et al. |
| 2007/0149993 A1 | 6/2007 | Kasahara et al. |
| 2007/0185453 A1 | 8/2007 | Michael et al. |
| 2007/0191759 A1 | 8/2007 | Stoller et al. |
| 2007/0204890 A1 | 9/2007 | Torii |
| 2007/0225566 A1 | 9/2007 | Kawanishi |
| 2007/0244361 A1 | 10/2007 | Ikeda et al. |
| 2008/0009797 A1 | 1/2008 | Stellon et al. |
| 2008/0249475 A1 | 10/2008 | Albrecht et al. |
| 2008/0269696 A1 | 10/2008 | Exline et al. |
| 2009/0005799 A1 | 1/2009 | Franer et al. |
| 2009/0093682 A1 | 4/2009 | Izzo et al. |
| 2009/0137943 A1 | 5/2009 | Stearns et al. |
| 2009/0192444 A1 | 7/2009 | Albrecht et al. |
| 2009/0221960 A1 | 9/2009 | Albrecht et al. |
| 2009/0234293 A1 | 9/2009 | Albrecht et al. |
| 2009/0240204 A1 | 9/2009 | Taylor et al. |
| 2009/0264703 A1 | 10/2009 | Pribanic |
| 2009/0270681 A1 | 10/2009 | Moreno et al. |
| 2009/0270685 A1 | 10/2009 | Moreno et al. |
| 2009/0270813 A1 | 10/2009 | Moreno, Jr. et al. |
| 2009/0270817 A1 | 10/2009 | Moreno et al. |
| 2009/0281478 A1 | 11/2009 | Duke |
| 2009/0314422 A1 | 12/2009 | Racenet et al. |
| 2010/0022958 A1 | 1/2010 | Moreno, Jr. et al. |

FOREIGN PATENT DOCUMENTS

| | | |
|---|---|---|
| CA | 2661238 A1 | 10/2009 |
| DE | 3238832 C1 | 2/1984 |
| DE | 19619065 A1 | 11/1997 |
| DE | 10330518 A1 | 2/2005 |
| EP | 0517248 | 12/1992 |
| EP | 0567142 | 10/1993 |
| EP | 568383 A1 | 11/1993 |
| EP | 570802 A1 | 11/1993 |
| EP | 664101 A1 | 7/1995 |
| EP | 0696459 | 2/1996 |
| EP | 731718 B1 | 9/1996 |
| EP | 845960 B1 | 6/1998 |
| EP | 875256 B1 | 11/1998 |
| EP | 890342 B1 | 1/1999 |
| EP | 898971 B1 | 3/1999 |
| EP | 0972493 | 1/2000 |
| EP | 1210904 B1 | 6/2002 |
| EP | 1284664 | 2/2003 |
| EP | 1312318 B1 | 5/2003 |
| EP | 1323373 A3 | 7/2003 |
| EP | 1348386 | 10/2003 |
| EP | 1459688 | 9/2004 |
| EP | 1629787 A2 | 3/2006 |
| EP | 1679043 | 7/2006 |
| EP | 1698291 | 9/2006 |
| EP | 1707133 | 10/2006 |
| EP | 1709918 | 10/2006 |
| EP | 1834571 A1 | 9/2007 |
| EP | 1834573 A1 | 9/2007 |
| GB | 2298906 A | 9/1996 |
| JP | 61036718 A2 | 2/1986 |
| JP | 3106329 A2 | 5/1991 |
| JP | 4020324 A2 | 1/1992 |
| JP | 4158825 A2 | 6/1992 |
| JP | 4170929 A2 | 6/1992 |
| JP | 4329510 A2 | 11/1992 |
| JP | 519997 A2 | 8/1993 |
| JP | 5192294 A2 | 8/1993 |
| JP | 5207962 A2 | 8/1993 |
| JP | 6133927 A2 | 5/1994 |
| JP | 6169879 A2 | 6/1994 |

| | | |
|---|---:|---|
| JP | 6304121 A2 | 11/1994 |
| JP | 7178039 A2 | 7/1995 |
| JP | 7246187 A2 | 9/1995 |
| JP | 7289501 A2 | 11/1995 |
| JP | 7313442 A2 | 12/1995 |
| JP | 8154888 A2 | 6/1996 |
| JP | 8173372 A2 | 7/1996 |
| JP | 10043128 A2 | 2/1998 |
| JP | 11146882 A2 | 6/1999 |
| JP | 2002224014 B2 | 8/2002 |
| JP | 2002238906 A2 | 8/2002 |
| JP | 2003284686 A2 | 10/2003 |
| JP | 2004016455 A2 | 1/2004 |
| JP | 2004267583 A2 | 9/2004 |
| JP | 2005253543 A2 | 9/2005 |
| JP | 2005319101 A2 | 11/2005 |
| JP | 2009261923 A | 11/2009 |
| WO | WO-9407552 | 4/1994 |
| WO | WO-9604946 A1 | 2/1996 |
| WO | WO-9740759 A1 | 11/1997 |
| WO | 9809673 A1 | 3/1998 |
| WO | WO-0189371 A1 | 11/2001 |
| WO | WO-02078527 A2 | 10/2002 |
| WO | WO-02096307 A2 | 12/2002 |
| WO | WO-03011154 A2 | 2/2003 |
| WO | WO-2004043275 A1 | 5/2004 |
| WO | WO-2005016133 A1 | 2/2005 |
| WO | 2005030293 A2 | 4/2005 |
| WO | WO-2005097019 A2 | 10/2005 |
| WO | WO-2005097234 A2 | 10/2005 |

OTHER PUBLICATIONS

U.S. Appl. No. 11/771,263, Franer et al.

* cited by examiner

VIBRATORY TROCAR

FIELD OF THE INVENTION

The present invention relates to methods and devices for performing surgical procedures, and in particular to methods and devices for maintaining visibility during surgical procedures.

BACKGROUND OF THE INVENTION

During laparoscopic surgery, one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. During such procedures, a scoping device, such as an endoscope or laparoscope, is inserted through one of the trocars to allow a surgeon to view the operative field on an external monitor coupled to the scoping device.

Scoping devices are often inserted and removed through a trocar multiple times during a single surgical procedure, and during each insertion and each removal they can encounter fluid that can adhere to the scope's lens and fully or partially impede visibility through the lens. Furthermore, a scope can draw fluid from inside or outside a patients body into the trocar, where the fluid can be deposited within the trocar until the scope or other instrument is reinserted through the trocar. Upon reinsertion, fluid can adhere to the scope's lens. The scope's lens thus needs to be cleaned to restore visibility, often multiple times during a single surgical procedure. With limited access to a scope in a body, each lens cleaning can require removing the scope from the body, cleaning the scope lens of fluid, and reintroducing the scope into the body. Such lens cleaning is a time-consuming procedure that also increases the chances of complications and contamination through repeated scope insertion and removal.

Accordingly, there is a need for methods and devices for maintaining clear visibility through a lens of a scoping device during a surgical procedure.

SUMMARY OF THE INVENTION

The systems and methods disclosed herein can be useful to maintain surgical viewing devices, and the trocars through which they are inserted, free of fluid that might otherwise impair visibility through the viewing device. In one embodiment, a method for removing fluid from a trocar is provided. The method can include positioning a trocar to extend into a body cavity and vibrating the trocar to prevent fluid in the trocar from being deposited on surgical instruments, such as surgical viewing devices (e.g., endoscopes and laparoscopes), passed therethrough.

In certain exemplary embodiments, vibrating the trocar can cause fluid deposited on at least one seal disposed within the trocar to be dislodged from the seal. Vibrating the trocar can further cause the dislodged fluid to pass into a cannula of the trocar. The trocar can be vibrated after an instrument is removed from the trocar, and/or while an instrument is passed through the trocar. Vibration can also be sensor activated. For example, the trocar can be selectively vibrated according to an output of a sensor that detects the presence of an instrument in the trocar. A sensor can also or alternatively detect the presence of fluid at a location within the trocar and an indicator can be selectively activated according to an output of the sensor. An output of a sensor that detects the presence of fluid at a location within the trocar can also be used to selectively vibrate the trocar. The trocar can be vibrated in a variety of ways. For example, the trocar can be vibrated by activating a transducer or by activating a mechanical vibrator. In one embodiment, the transducer can be activated by activating a foot pedal coupled to the transducer or by a remote control.

In another embodiment, a method for removing fluid from a trocar is provided that can include activating a transducer coupled to a trocar inserted into a body cavity to vibrate the trocar and remove fluid deposited on at least one seal in the trocar by an instrument passed therethrough. Vibration can cause fluid to pass from the at least one seal into a cannula of the trocar.

In yet another embodiment, a method for removing fluid from an endoscope is provided. The method can include inserting a trocar through tissue to form a working channel extending through the trocar into a body cavity. The method can further include passing an endoscope through the trocar and vibrating the trocar to remove any fluid deposited within the trocar by the endoscope. The trocar can be vibrated, for example, ultrasonically or mechanically.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

A person skilled in the art will appreciate that, while the methods and devices are described in connection with minimally invasive procedures, such as endoscopic and laparoscopic procedures, the methods and devices disclosed herein can be used in numerous surgical procedures. By way of non-limiting example, the devices can be used in laparoscopic procedures, in which the device is introduced percutaneously, and more preferably through an introducer, such as a cannula or trocar. The methods and devices can also be used in open surgical procedures.

In general, devices and methods are provided for removing fluid from a trocar and/or from surgical instruments passed therethrough, and for preventing such fluid from accumulating. For example, in one exemplary embodiment, fluid can be removed from a trocar by positioning a trocar to extend into a body cavity and vibrating the trocar to prevent fluid in the trocar, or fluid on instruments disposed in the trocar, from being deposited on surgical instruments passed therethrough. This will allow instruments, such as viewing devices, to be repeatedly passed through the trocar without fluid being deposited on a lens of the viewing instrument.

A person skilled in the art will appreciate that the term fluid as used herein is intended to include any substance that, when on a surgical instrument, can adversely affect the functioning of the instrument or a surgeon's ability to use it. Fluids include any kind of bodily fluid, such as blood, and any kind of fluid introduced during a surgical procedure, such as saline. Fluids also include fluid/solid mixtures or fluids with particles (such as pieces of tissue) suspended or located therein, as well as viscous materials and gases.

Figure 1:
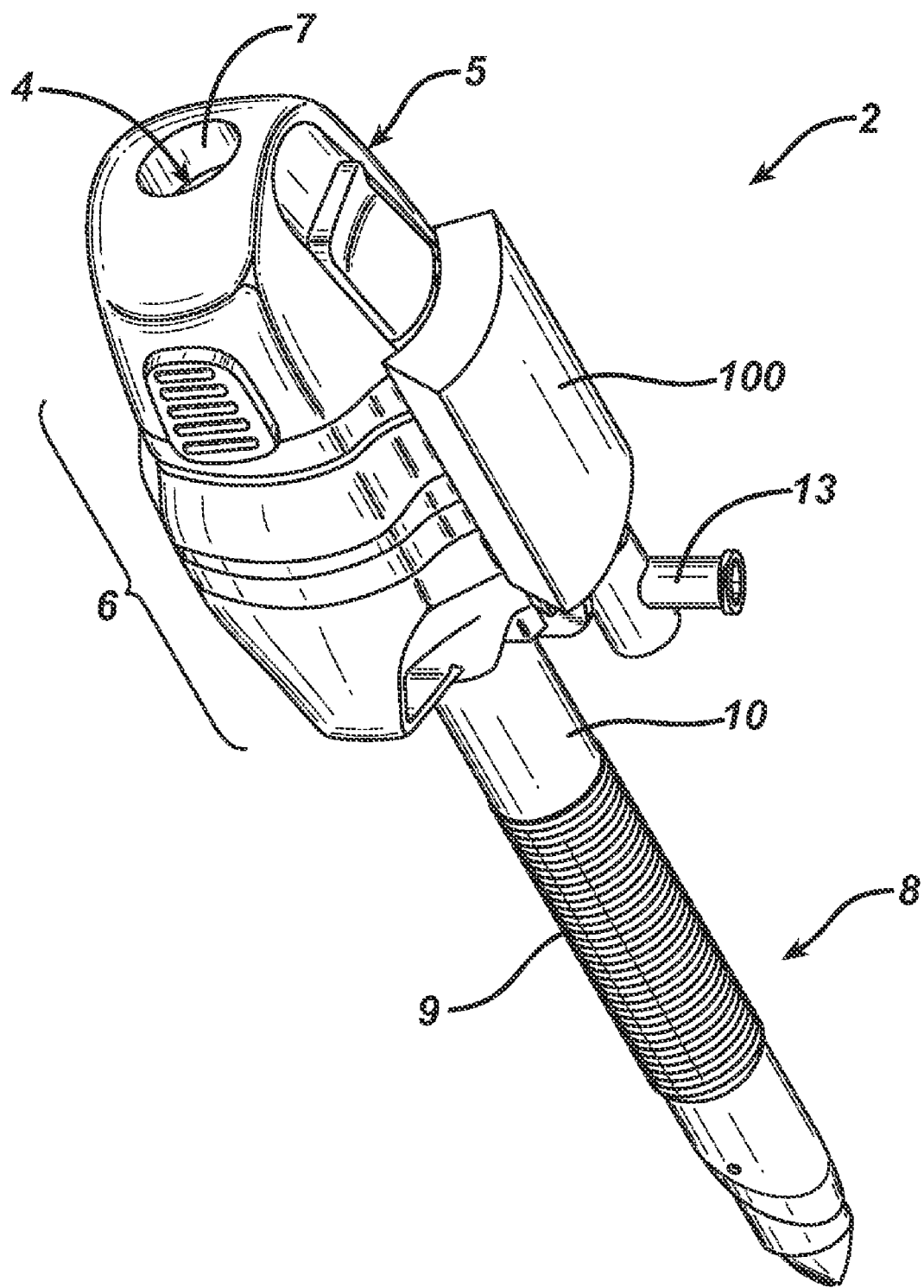
FIG. 1 is a perspective view of one exemplary embodiment of a vibratory trocar device having an elongate body and a transducer housing.
Figure 2:
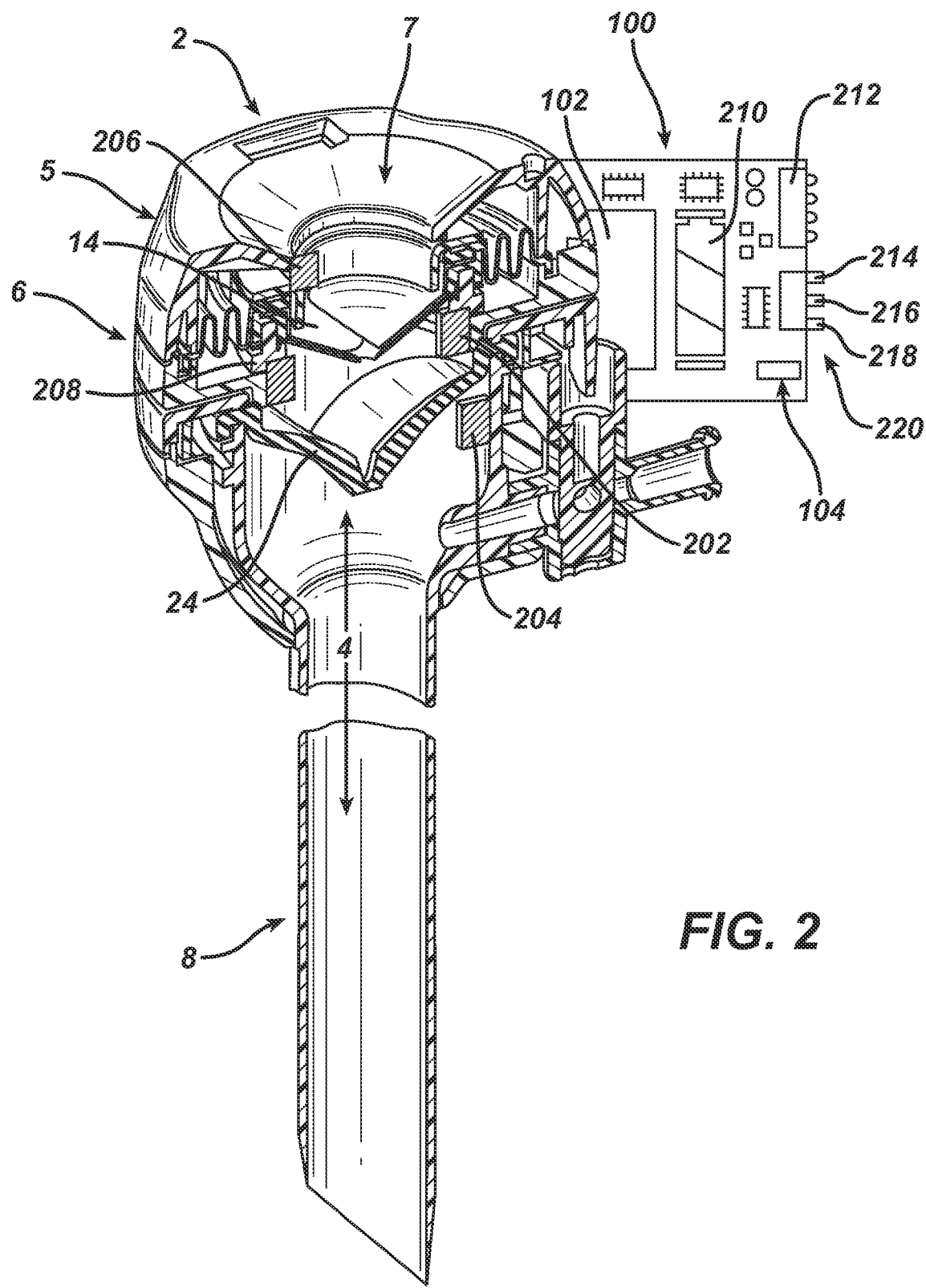
FIG. 2 is a cross-sectional perspective view of the vibratory trocar device of FIG. 1 showing a plurality of seals in the working channel and a transducer and associated transducer control circuitry.

While the techniques for removing fluid disclosed herein can be used with various devices known in the art, in certain exemplary embodiments a trocar is provided having one or more vibrator elements disposed therein or thereon for removing fluid from portions of the trocar and/or from an instrument, such as a scoping device, inserted therethrough. FIGS. 1 and 2 illustrate one exemplary embodiment of a vibratory trocar device 2. As shown, the vibratory trocar device 2 is generally in the form of a housing having a proximal portion 6 (also referred to herein as a proximal housing) that can house one or more sealing elements and a distal cannula 8 extending distally from the proximal housing 6 and configured to be disposed through tissue to extend into a body cavity. The vibratory trocar device 2 defines a working channel 4 extending therethrough for introducing various instruments into a body cavity. A number of configurations are available for the proximal housing 6. In the illustrated embodiment, the proximal housing 6 has a generally cylindrical shape with a removable cap portion 5. An opening 7 can be formed in the proximal end of the housing 6 such that the opening 7 extends through the removable cap 5 and is coaxial with the working channel 4 extending through the housing 6 and the cannula 8. The housing 6 can also include other features, such as a stop-cock valve 13 for allowing and preventing the passage of an insufflation fluid, e.g. carbon dioxide, through the vibratory trocar device 2 and into a body cavity. The cannula 8 can also have various configurations, and can include various features known in the art. In the illustrated embodiment, the cannula 8 has a generally elongate cylindrical shape and includes a series of annular tissue-engaging ridges 9 formed on an external surface 10 thereof. One skilled in the art will appreciate that the housing 6 and the cannula 8 can be formed as a unitary structure or as two separate components that are mated to one another.

In use, the distal cannula 8 can be inserted through a skin incision and through tissue to position a distal-most end within a body cavity. The proximal housing 6 can remain external to the body cavity, and various instruments can be inserted through the working channel 4 and into the body cavity. Typically, during surgical procedures in a body cavity, such as the abdomen, insufflation is provided through the vibratory trocar device 2 to expand the body cavity to facilitate the surgical procedure. Thus, in order to maintain insufflation within the body cavity, most trocars include at least one seal disposed therein to prevent air from escaping. Various seal configurations are known in the art, but typically the vibratory trocar device 2 includes an instrument seal that forms a seal around an instrument inserted therethrough, but otherwise does not form a seal when no instrument is inserted therethrough; a trocar seal or zero-closure seal that seals the working channel 4 when no instrument is inserted therethrough; or a combination instrument seal and trocar seal that is effective to both form a seal around an instrument inserted therethrough and to form a seal in the working channel 4 when no instrument is inserted therethrough. In the embodiment shown in FIGS. 1 and 2, the vibratory trocar device 2 includes an instrument seal 14 and a separate trocar or zero-closure seal 24. However, a person skilled in the art will appreciate that various other seals known in the art can be used including, for example, flapper valves, gel seals, diaphragm seals, etc.

Figure 3:
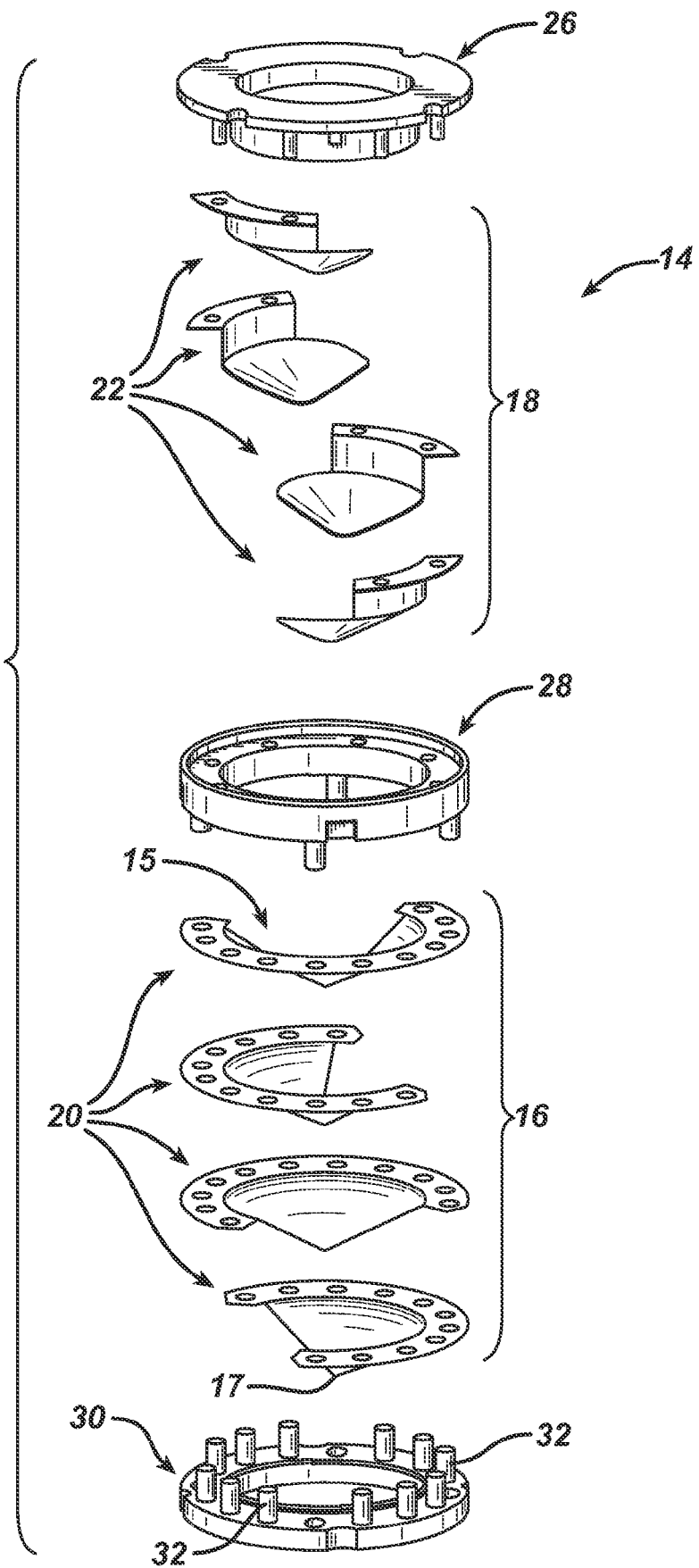
FIG. 3 is an exploded perspective view of an instrument seal shown in FIG. 2.

The instrument seal 14 is shown in more detail in FIG. 3 and, as shown, is generally in the form of a multi-layer conical seal 16 and a multi-layer protective member 18 disposed on a proximal surface 15 of the seal 16. The multi-layer conical seal 16 can include a series of overlapping seal segments 20 that are assembled in a woven arrangement to provide a complete seal body. The seal segments 20 can be stacked on top of one another or woven together in an overlapping fashion to form the multi-layer seal 16 having a central opening 17 therein. The seal segments 20 can be made from any number of materials known to those skilled in the art, but in an exemplary embodiment the seal segments 20 are formed from an elastomeric material. The seal segments 20 can also be molded such that they have a varying thickness across the profile of the seal 16. Varying the thickness across to the profile of the seal 16 can be effective to minimize leakage and reduce drag forces on the instrument. The multi-layer protective member 18 can similarly be formed from a series of overlapping segments 22 that are disposed proximal to the overlapping seal segments 20 and that are configured to protect the seal segments 20 from damage caused by surgical instruments inserted through the opening 17 in the seal 16. The protective member 18 can also be formed from various materials, but in certain exemplary embodiments the protective member 18 is formed from a molded thermoplastic elastomer. The segments 20, 22 that form the seal 16 and the protective member 18 can be held together using various techniques known in the art. As shown in FIG. 3, the segments 20, 22 are held together by several ring members that mate to engage the segments 20, 22 therebetween. In particular, the protective member 18 is engaged between a crown 26 and a gasket ring 28, and the seal 16 is engaged between the gasket ring 28 and a retainer ring 30. Pins 32 are used to mate the ring members 26, 28 and to extend through and engage the segments of the seal 16 and the protective member 18.

When fully assembled, the instrument seal 14 can be disposed at various locations within the vibratory trocar device 2. In the embodiment illustrated in FIG. 2, the instrument seal 14 is disposed in the cap 5 of the vibratory trocar device 2 at a location just distal of the proximal opening 7 and proximal of a trocar seal 24. In use, an instrument can be inserted into the center of the seal assembly and the seal segments 20, 22 can engage and form a seal around an outer surface of the instrument to thereby prevent the passage of fluids through the seal 14. When no instrument is inserted therethrough, the opening will not form a seal in the working channel 4, however other configurations in which a seal is formed when no instrument is inserted therethrough are also conceivable. Exemplary instrument seal configurations are described in more detail in U.S. Publication No. 2004/0230161 entitled "Trocar Seal Assembly," filed on Mar. 31, 2004, and U.S. Publication No. 2007/0185453 entitled "Conical Trocar Seal," filed on Oct. 15, 2003, which are hereby incorporated by reference in their entireties.

Figure 4:
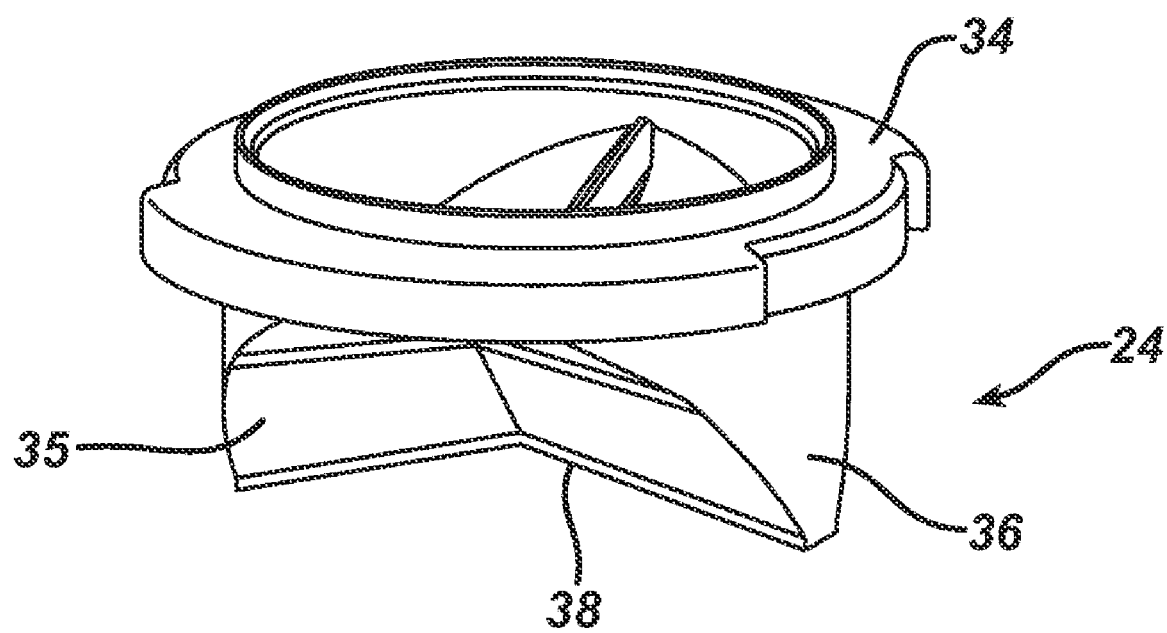
FIG. 4 is a perspective view of a trocar seal shown in FIG. 2.

The trocar or zero-closure seal in the illustrated embodiment is shown in more detail in FIG. 4, and as shown the illustrated zero-closure seal is in the form of a duckbill seal 24. The seal 24 is configured to form a seal in the working channel 4 when no instrument is inserted therethrough to thus prevent the leakage of insufflation gases delivered through the vibratory trocar device 2 to the body cavity. As shown, the duckbill seal 24 has a generally circular flange 34 with a sidewall 36 extending distally therefrom. The shape of the sidewall 36 can vary, but in the illustrated embodiment, the sidewall 36 includes opposed flaps 35 that extend at an angle toward one another in a distal direction and that come together at a distal end to form a seal face 38. The opposed flaps 35 are movable relative to one another to allow the seal face 38 to move between a closed position, in which no instrument is inserted therethrough and the seal face 38 seals the working channel 4 of the vibratory trocar device 2, and an open position in which an instrument is inserted therethrough. The seal can include various other features, as described in more detail in U.S. Publication No. 2009/0005799 entitled "Duckbill Seal with Fluid Drainage Feature," filed on Jun. 29, 2007, which is hereby incorporated by reference in its entirety.

In accordance with the present disclosure the general structure of the seals as well as the trocar do not generally form part of the present invention. As such, a person skilled in the art will certainly appreciate that various seal configurations, as well as various trocars or other surgical access devices, can be used without departing from the spirit of the invention disclosed herein.

As previously indicated, the vibratory trocar device 2 can also be configured to remove fluid from the trocar, or certain portions thereof, and/or from instruments inserted therethrough. Any device effective to vibrate the trocar device 2 or an instrument therein can be used, such as ultrasonic or mechanical vibration devices. For example, in one embodiment, a small DC motor can be mounted within a housing that is disposed in or coupled to the vibratory trocar device 2. When activated, the motor can rotate a gear attached to the motor's drive shaft. A small weight can be coupled to the gear in an off-center fashion such that the rotating assembly is unbalanced. When the motor is activated to rotate the gear/weight combination, the unbalanced rotation generates a mechanical vibration that, when applied to the vibratory trocar device 2, is effective to remove fluid therefrom. In an exemplary embodiment, the motor rotates at 100 to 150 rotations per minute and the weight has a mass of approximately 25 grams.

Figure 5:
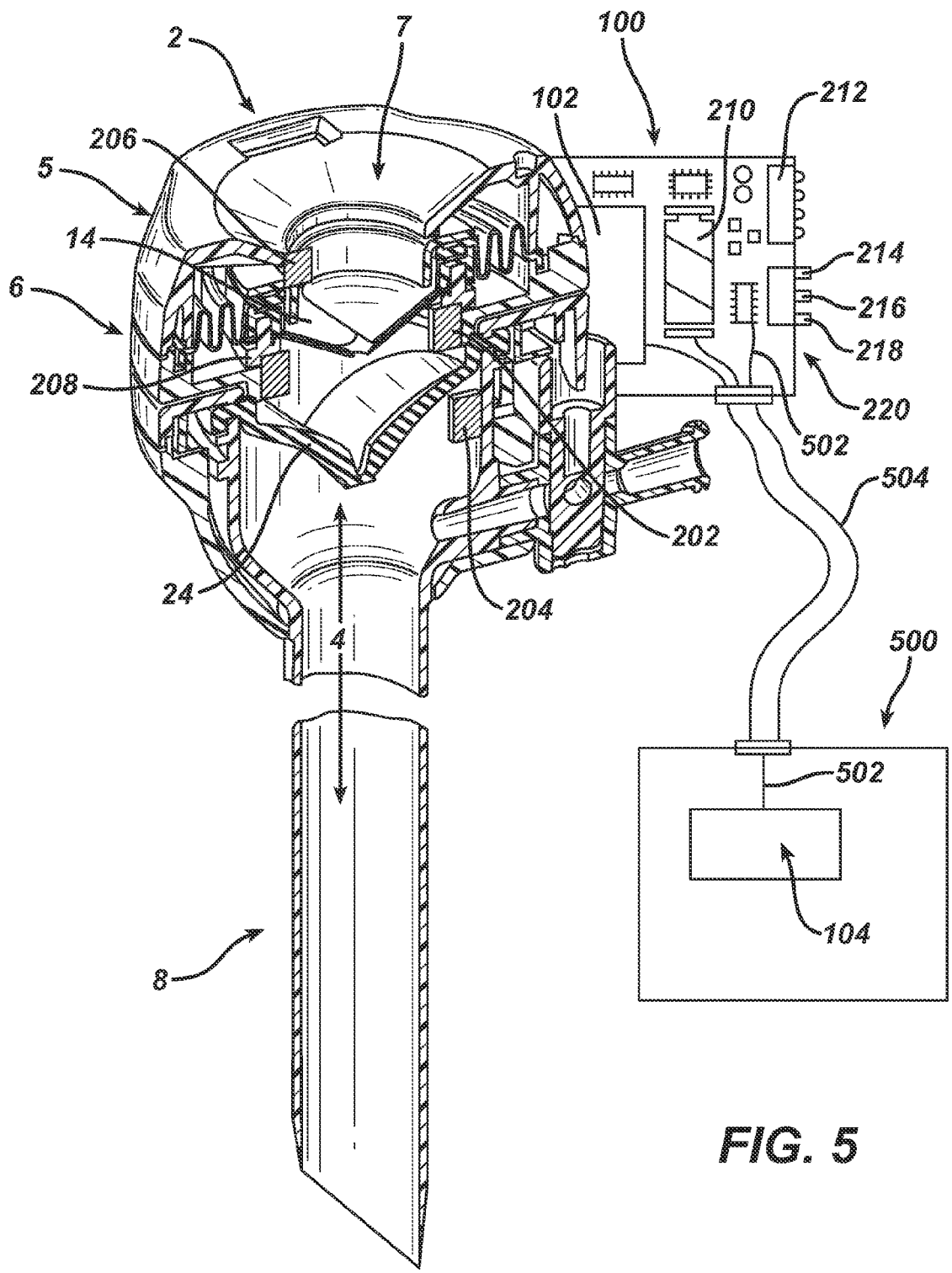
FIG. 5 is a cross-sectional perspective view of the vibratory trocar device of FIG. 1 having transducer control circuitry housed separately from the vibratory trocar device.

Alternatively, or in addition, a transducer can be used to vibrate the vibratory trocar device 2. In the embodiment shown in FIGS. 1 and 2, the vibratory trocar device 2 includes a transducer housing 100. A transducer 102 and associated transducer control circuitry 104 can be housed within the transducer housing 100. In other embodiments, as shown in FIG. 5, the transducer control circuitry 104 can be located in a separate transducer control box 500.

Referring to FIG. 2, the transducer 102 can be placed in several different locations on or within the vibratory trocar device 2, and it can have a variety of shapes and sizes. In the illustrated embodiment, the transducer 102 is in the form of a generally rectangular housing that is mated to an external sidewall of the housing 6 in proximity to the seals 14, 24. In other embodiments, the transducer 102 can be coupled to a proximal surface of the housing 6 or the cannula 8, or it can be disposed within the housing 6 and/or the cannula 8. The range of shapes and sizes that can be chosen for the transducer is broad. For example, in one embodiment the transducer can be ring shaped such that it substantially surrounds the housing 6, the cannula 8, and/or the working channel 4. In another embodiment, the transducer 102 can instead have a small conical tip that is placed into contact with certain portions of the vibratory trocar device 2, such as one or both of the seals 14, 24. In such a configuration, the relatively small contact area between the transducer tip and the device 2 (or portions thereof) can permit more precise or localized application of vibratory forces.

The transducer 102 can be coupled to the vibratory trocar device 2 in a variety of ways. For example, the transducer 102 can be permanently affixed to the vibratory trocar device 2 or it can be removably attached thereto. The transducer can be manually held against the vibratory trocar device 2 or it can be welded, molded, or glued thereto. Alternatively, or in addition, screws, bolts, clips, tape or other fastening techniques known in the art can also be employed. In one embodiment, the transducer 102 can be formed integrally with the vibratory trocar device 2.

The transducer control circuitry 104 can have a variety of configurations, but in one embodiment, the control circuitry 104 can be configured to selectively produce an alternating voltage across one or more piezoelectric crystals in the transducer 102, causing the crystals to resonate and produce very high frequency sound waves. In certain embodiments, the frequency of the sound waves is in the ultrasonic range. The emission of high frequency sound waves from the transducer 102 causes the vibratory trocar device 2, or at least portions thereof, to vibrate or otherwise agitate. As will be discussed in more detail below, vibration of the vibratory trocar device 2 can cause fluid deposited on the seals 14, 24 and/or elsewhere inside the housing 6, the cannula 8, and/or on instruments disposed in the trocar, to dislodge. Once dislodged, gravitational forces can cause the fluid to move towards the distal end of the cannula 8, thereby providing a clear pathway for instruments to be passed through the vibratory trocar device 2.

As will be discussed further below, the transducer can be selectively activated in any number of ways, including by one or more switches, foot pedals, remote controls, computers, sensors, or any other activation mechanisms known in the art.

As further shown in FIG. 2, the vibratory trocar device 2 can also include one or more sensors disposed therein and configured to detect the presence of fluid and/or instruments within the vibratory trocar device 2. In the illustrated embodiment, the vibratory trocar device 2 includes four sensors 202, 204, 206, 208. The vibratory trocar device 2 can, however, include any number of sensors disposed therein or thereon.

As shown, a proximal fluid sensor 202 is mounted inside the housing 6 near the proximal multi-layer instrument seal 14, and a distal fluid sensor 204 is mounted near the distal duck-bill trocar seal 24. The proximal and distal fluid sensors 202, 204 can detect the presence of fluid within the working channel 4 in the vicinity of the seals 14, 24, respectively. The vibratory trocar device 2 can also include proximal and/or distal instrument sensors 206, 208. The instrument sensors 206, 208 can detect the presence of an instrument or other object in the working channel 4. In other embodiments, different sensor configurations can be employed. For example, multiple sensors can be positioned to detect fluid in the vicinity of the same seal and some seals can have many sensors nearby, while others can have none. The sensors 202, 204, 206, 208 can be mounted within the vibratory trocar device 2 using a variety of techniques known in the art.

The sensors 202, 204, 206, 208 can also be chosen from wide array of sensor types. For example, optical, mechanical, electromagnetic, or thermal sensors can be used. In an exemplary embodiment, the sensors 202, 204, 206, 208 are proximity sensors specifically tailored to detect the presence of nearby objects (i.e. fluid or surgical instruments). The sensors 202, 204, 206, 208 can emit an electromagnetic field, an electrostatic field, or a beam of electromagnetic radiation. As an instrument is introduced into or removed from the working channel 4, or as fluid accumulates near or moves away from the sensors 202, 204, 206, 208, changes in the field or return signal can be measured by the sensor. Upon measuring such an alteration, an output of the sensor can be changed. In embodiments where the sensor includes an analog output, the voltage on the sensor's output wire, pin, and/or terminal can be increased or decreased in a manner commensurate with the change in field or return signal. In embodiments where the sensor includes a digital output, the output can be asserted, cleared, and/or toggled. One skilled in the art will recognize that some sensor types are better suited than others for detecting objects of a given size or material. Accordingly, the sensors 202, 204, 206, 208 can be of different types, sizes, and/or tolerances depending on whether they are used for detecting fluid and/or for detecting the presence of instruments. Additionally, fluid, as defined herein, can have a broad range of properties and compositions, so in some embodiments, multiple sensors of varying types can be used to better detect the presence of fluid.

Referring still to FIG. 2, the transducer housing 100 can also include various other components necessary for operation, such as a battery 210, an LED indicator bank 212, a power switch 214, an auto/manual switch 216, and/or a vibration switch 218. The switches 214, 216, 218 and/or the LED indicator bank 212 can be visible and/or accessible from the outside of the transducer housing 100 and can be electrically coupled to the transducer control circuitry 104. A label 220 can also be applied to the exterior of the transducer housing 100 to identify to a user the function of each of the switches 214, 216, 218 and the LED indicator bank 212. The switches 214, 216, 218 can be push-buttons, slide switches, rotatable knobs, or any other type of switch known in the art. When the power switch 214 is activated, a current path is formed, electrically connecting the battery 210 to the transducer control circuitry 104 and supplying power thereto. The transducer control circuitry 104 can in turn supply power to the sensors 202, 204, 206, 208, the LED indicator bank 212, and the transducer 102. The LED indicator bank 212 can include multiple LEDs for indicating various states of the device. For example, one LED in the LED indicator bank 212 can be illuminated to indicate that the battery power is low. Others can be illuminated to indicate that fluid is present in the working channel 4, or that the vibratory trocar device 2 is powered on.

In use, outputs from the sensors 202, 204, 206, 208 can be electrically coupled or otherwise communicated to the transducer control circuitry 104 which can include a printed circuit board and various logic components or integrated circuits. The transducer control circuitry 104 can condition and interpret the outputs from the sensors 202, 204, 206, 208 and based thereon, selectively activate the transducer 102 or each individual LED within the LED indicator bank 212. In another embodiment, shown in FIG. 5, where the transducer control circuitry 104 is located in a separate transducer control box 500, in order to activate the transducer 102, the transducer control circuitry 104 can send a signal to the transducer 102. The signal can be sent wirelessly using devices and methods known in the art or a hard-wired electrical connection between the controller unit 104 and the transducer 102 can be used. In the case of a hard-wired electrical connection, the transducer control circuitry 104 can be electrically coupled to the transducer 102 using one or more conductive wires 502 housed in a cable 504. The cable 504 can house other conductive wires or insulating materials that can be used for a variety of purposes, such as providing power, grounding, shielding, or one or more communication paths between the vibratory trocar device 2 and the transducer control circuitry 104.

Referring back to FIG. 2, in one embodiment, the auto/manual switch 216 can be set to one of two positions—"auto" and "manual." The positions can be indicated on the label 220. When the auto/manual switch 216 is in the "auto" position, the transducer control circuitry 104 can activate the transducer 102 to vibrate the device 2 whenever the fluid sensors 202, 204 indicate that fluid is present in the working channel 4 or on the seals 14, 24. As stated earlier, this vibration of the device 2 can dislodge the fluid and cause it to move away from the seals 14, 24 or the working channel 4. In such an embodiment, the transducer control circuitry 104 can keep the transducer 102 active as long as is required to clear the fluid. To accomplish this, the transducer control circuitry 104 can activate the transducer 102 until the output of all fluid sensors indicate that no fluid or insufficient fluid is present.

In another embodiment, if the output of the instrument sensors 206, 208 indicates that an object is being passed (i.e. inserted or removed) through the working channel 4, the transducer control circuitry 104 can selectively activate the transducer 102 to ensure that the instrument is not contaminated with fluid. For example, if a viewing device or scope is passed into the working channel 4, the presence of the scope can be detected by the sensor 206 just before the scope is inserted through the proximal seal 14. The sensor 206 can then change its output to indicate that an instrument is being introduced into the channel, which can in turn cause the transducer control circuitry 104 to activate the transducer 102. In this case, the transducer 102 can be activated briefly (e.g. for a predetermined period of time) to dislodge any fluid that might exist within the working channel 4 before the scope is passed through the seal 14, thereby providing a clear entry path for the scope.

When the auto/manual switch 216 is in the "manual" position, the transducer control circuitry 104 can only activate the transducer 102 to vibrate the device 2 whenever a user activates the vibration switch 218. If the sensors 202, 204, 206, 208 indicate that fluid is present or that an object is being passed through the device, the controller unit will only illuminate the LEDs in the LED indicator bank 212 to alert the user to this condition. Once alerted, the user can decide when activation of the transducer 102 is desired and can use the vibration switch 218 to selectively activate the transducer 102. Accordingly, the "manual" setting can be desirable when non-viewing devices are present in the device or when performing critical steps in a surgical operation since in these circumstances, unplanned vibration can be undesirable or even harmful to the instruments or the patient.

In another embodiment, the transducer housing 100 can also include a communications port for interfacing with a computer. The communications port can be electrically coupled to a computer using wires or can communicate wirelessly with a computer. The communications port can be electrically coupled to the transducer control circuitry 104 and can permit a software application running on the computer to monitor and log the activity of the transducer control circuitry 104 and/or the vibratory trocar device 2. Identifying information, such as a serial number, can be communicated from the device 2 to the computer using the communications port. Based on the identifying information, the computer can keep a log or provide the user with information such as how often the vibratory trocar device 2 has been used, how long it has been used, when it was first used, when it was last used, how many times it has been vibrated, etc. The communications port can utilize a USB, RS232, TCP/IP, I2C, or any other communications standard known in the art.

In other embodiments, a foot pedal, remote control, or other device can be employed to manually activate the vibratory trocar device 2. A foot pedal can be desirable where the user wishes to keep both hands free for performing other surgical tasks, yet still be capable of manually activating the transducer 102. A remote control can be desirable if the user wishes to activate the transducer 102 without being close enough to the vibratory trocar device 2 to reach the switches on the transducer housing 100, for example where the user is a surgical assistant working from a far side of the operating room.

Figure 6:
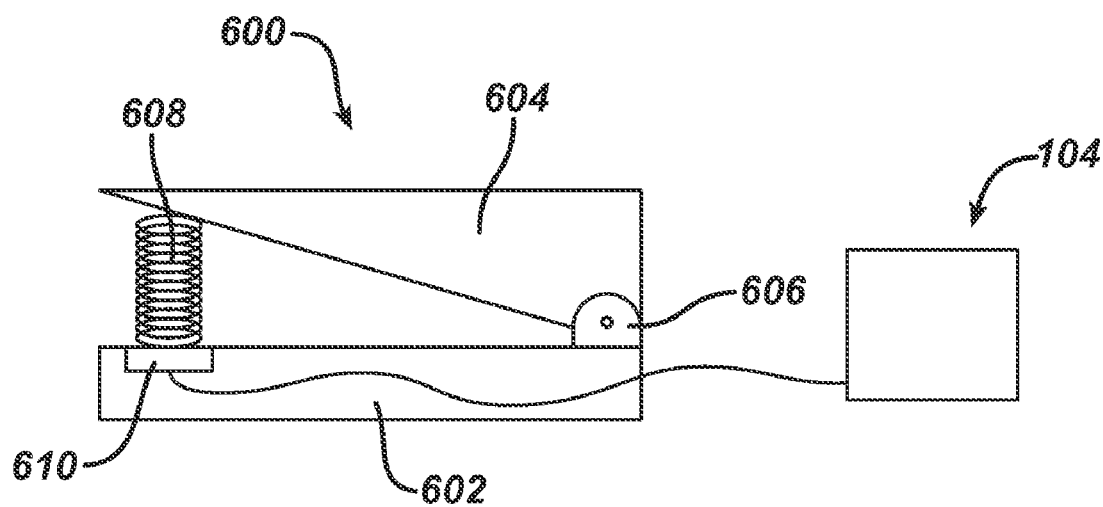
FIG. 6 is a schematic view of a foot pedal that can selectively activate a transducer of a vibratory trocar device.

FIG. 6 illustrates one embodiment of a foot pedal 600 that is electrically coupled to the transducer control circuitry 104. In the illustrated embodiment, the foot pedal 600 includes a base 602, a pedal 604, a pivot 606, a spring 608, and a pedal position sensor 610. The output of the sensor 610 can be read by the transducer control unit 104. The output of the pedal position sensor 610 can be a simple "on" or "off" type, in which case the transducer control circuitry 104 can activate the transducer 102 as soon as the pedal 604 is depressed towards the base 602 beyond a threshold point. As the user reduces or removes pressure from the pedal 604, the spring 608 causes the pedal 604 to move away from the base 602. As the pedal 604 moves away from the base 602, it eventually crosses the threshold point, causing the output of the pedal position sensor 610 to toggle and thereby cause the transducer control circuitry 104 to de-activate the transducer 102. The output of the sensor 610 can be communicated wirelessly to the transducer control circuitry 104 using techniques and devices known in the art, or can simply be communicated over traditional conductive wire.

Alternatively, the pedal position sensor 610 can be more sophisticated. For example, the output of the sensor 610 can be capable of communicating a multitude of pedal positions to the transducer control circuitry 104. The pedal position can be transmitted as an analog signal, or it can be transmitted digitally using a parallel or serial bus. When such a sensor is employed, the transducer control circuitry 104 can cause the transducer 102 to vibrate at different frequencies or amplitudes based on the position of the pedal 604. For example, as the pedal 604 is depressed towards the base 602 by the user, the vibrational frequency or vibrational amplitude of the transducer 102 can increase. As the user removes pressure from the pedal 604, the spring 608 begins to move the pedal 604 away from the base 602 and the frequency or amplitude of vibration of the transducer 102 can decrease. These embodiments can be desirable in applications where certain types of fluid are more easily dislodged using a higher frequency or amplitude of vibration while others are more easily removed using a lower frequency or amplitude.

Figure 7:
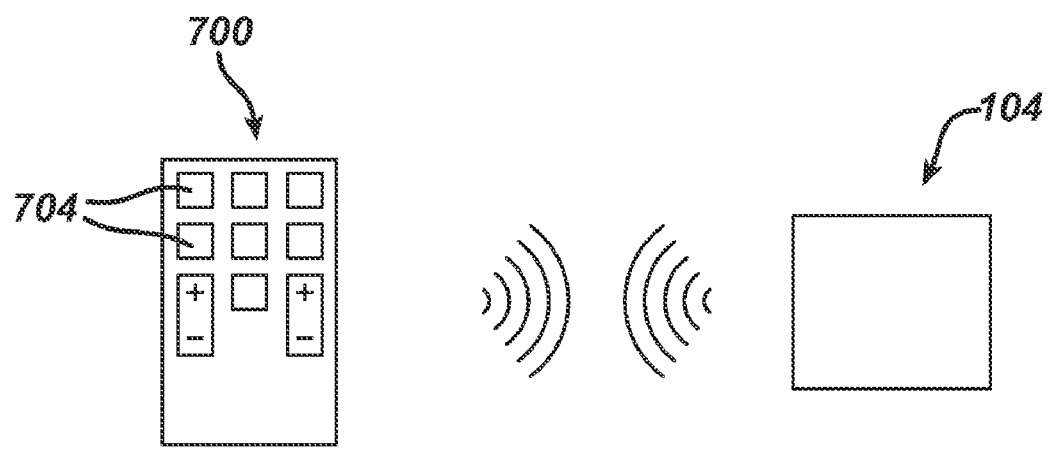
FIG. 7 is a schematic view of a remote control that can selectively activate a transducer of a vibratory trocar device.

In another embodiment, shown in FIG. 7, the vibratory trocar device can be used with a remote control 700. As shown, the remote control 700 has a plurality of buttons 704 and it can communicate wirelessly with the transducer control circuitry 104 using a suitable frequency in the infrared or RF spectrum. The remote control 700 can also be hard-wired to the transducer control circuitry 104. The buttons 704 on the remote control 700 can be assigned various functions such as activating and deactivating the transducer or adjusting the frequency and amplitude of vibration of the transducer.

In use, the trocar can be positioned to extend into a body cavity and can be vibrated to remove fluid from an instrument disposed therethrough, to prevent fluid in the trocar from being deposited on surgical instruments passed therethrough, and/or to prevent fluid from accumulating inside the trocar. For example, in a typical procedure, an incision can be formed in the patient and the distal end of a cannula 8 of the trocar can be advanced (e.g., using an obturator disposed through the trocar) through the incision and underlying tissue into a body cavity. Carbon dioxide gas can be introduced into the body cavity through the trocar to insufflate the body cavity. Surgical instruments and viewing devices such as endoscopes or laparoscopes can be passed through the trocar and into the body cavity to allow various procedures in or around the body cavity to be viewed on an external monitor. To prevent fluid from being deposited on the viewing instruments, and in particular to prevent fluid from contaminating the lenses of the viewing devices and thereby obstructing the image obtained by the viewing device, the trocar can be vibrated or otherwise agitated by activating the transducer 102.

Typically, during laparoscopic procedures, a viewing device or scope, such as a laparoscope or endoscope, is inserted through the working channel of a trocar to position a viewing element on the distal end of the scope within a body cavity. Upon removal of the scope, fluid from the body cavity can be dragged into the working channel of the trocar where it is deposited on the seals as they contact an outer surface of the scope. Thus, in an exemplary embodiment, in order to prevent the fluid on the seals from being re-deposited onto the scope or any other surgical instrument upon re-insertion through the trocar, the trocar can be vibrated to cause the fluid disposed within the trocar to be dislodged and to pass into the cannula of the trocar where it can drip, fall, or otherwise pass back into the body cavity. A person skilled in the art will appreciate that the trocar can be vibrated before passing the instruments therethrough to ensure that any fluid inside the trocar is cleared out of the way ahead of time. Alternatively, or in addition, the trocar can be vibrated while instruments are passed therethrough to remove fluid from the trocar and/or the instruments themselves. The trocar can also be vibrated after a surgical instrument is removed so that any fluid deposited within the trocar will be removed, thereby clearing the working channel of fluid before any other instruments are inserted.

Figure 8A:
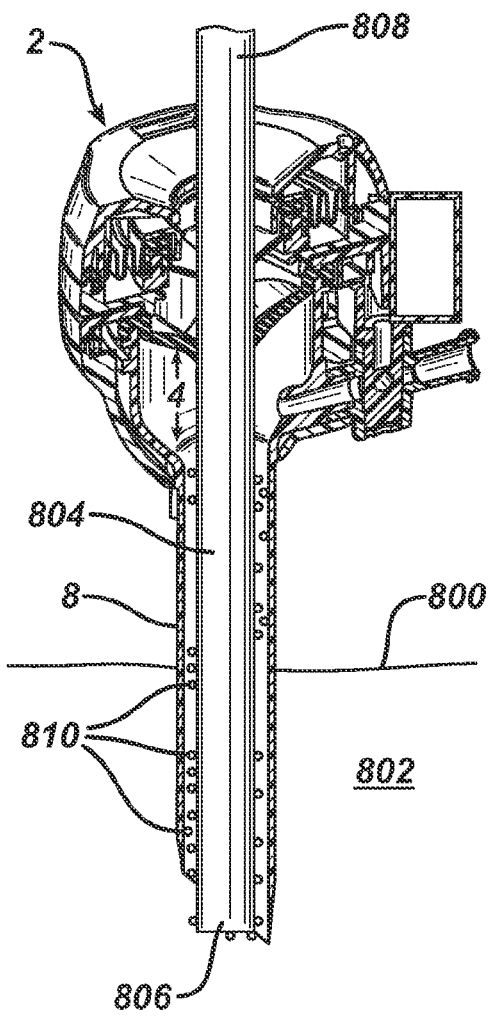
FIG. 8A is a cross-sectional perspective view of the vibratory trocar device of FIG. 1 showing a viewing device inserted in the working channel and fluid adhered to the viewing device.

FIGS. 8A-8D depict one exemplary method of removing fluid from a surgical access device. As shown in FIG. 8A, a vibratory trocar device 2 can be positioned such that the cannula 8 extends through a tissue layer 800 and into a body cavity 802 using methods known in the art. A scope 804 having a distal end 806 and a proximal end 808 can be inserted through the working channel 4 and into the body cavity 802. During the course of a surgical procedure, as the scope 804 is advanced, retracted, and otherwise moved about within body cavity 802, fluid 810 can adhere to the outer surface of the scope 804. A person skilled in the art will recognize that the fluid 810 is not drawn to scale and that the fluid can take a wide range of shapes, sizes, forms, and compositions.

Figure 8B:
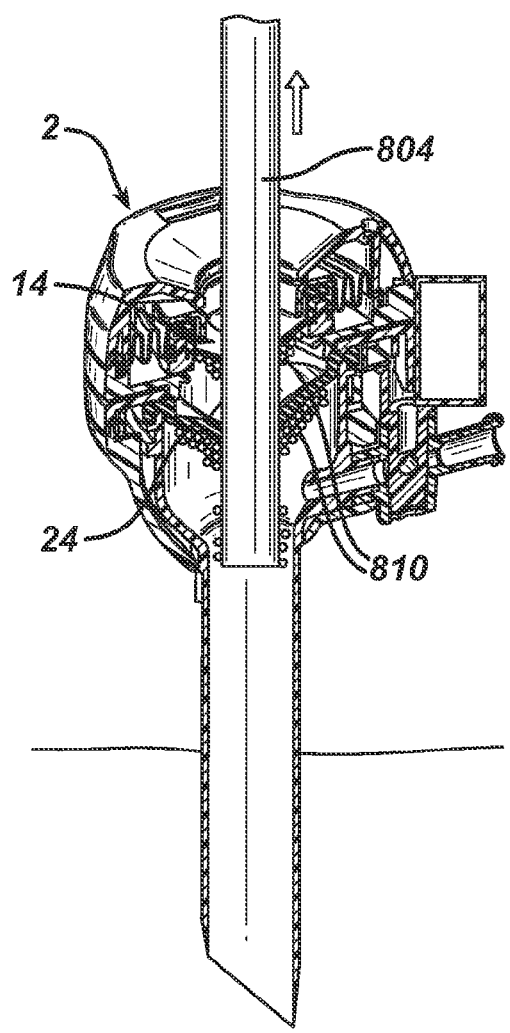
FIG. 8B is a cross-sectional perspective view of the vibratory trocar device of FIG. 8A showing the viewing device partially removed from the working channel.
Figure 8C:
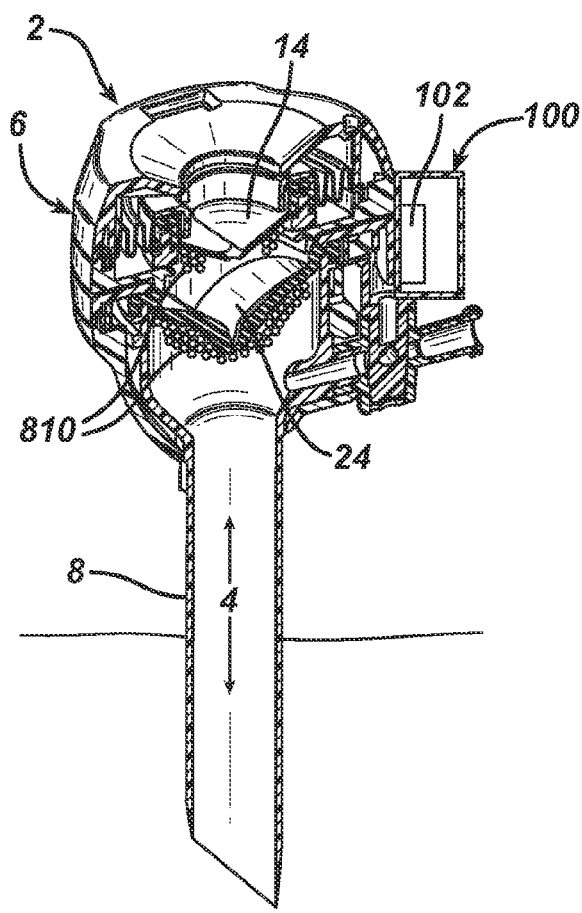
FIG. 8C is a cross-sectional perspective view of the vibratory trocar device of FIG. 8B showing fluid deposited on a seal by the removed viewing device.
Figure 8D:
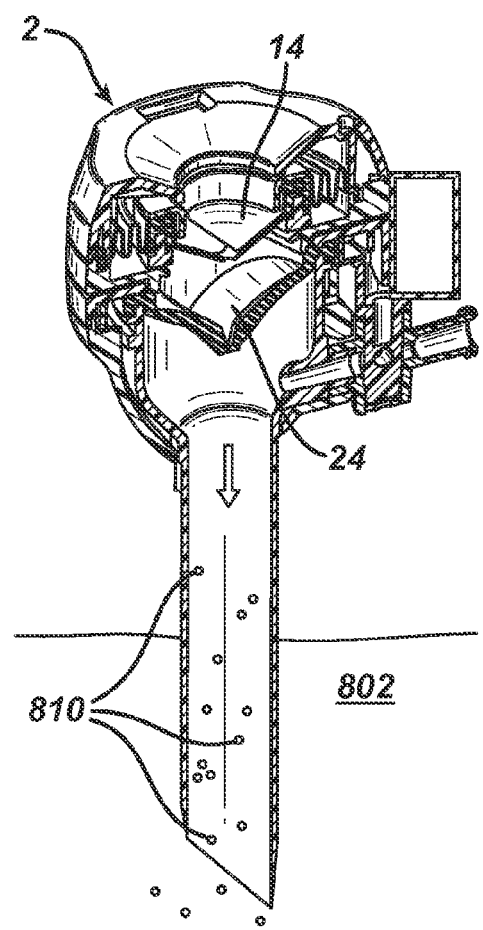
FIG. 8D is a cross-sectional perspective view of the vibratory trocar device of FIG. 8C showing fluid being removed from the working channel.

As shown in FIG. 8B, as the user withdraws the scope 804 distally from the vibratory trocar device 2, the fluid 810 adhered to the outer surface of the scope 804 will be transferred to the trocar seal 24 and can accumulate on a distal side of the trocar seal 24, along the seal opening, or at other locations on the seal depending on the seal configuration. Fluid can also accumulate on the instrument seal 14. Once the scope 804 is fully removed from the vibratory trocar device 2, as shown in FIG. 8C, the fluid 810 can be left behind on the trocar seal 24 and/or the instrument seal 14. In many cases, the fluid 810 can also be left behind on the inner walls of the cannula 8 or the housing 6, or on other interior portions of the vibratory trocar device 2. If the user takes no action to remove the fluid 810, it can be re-deposited on the leading surface or other outer surface of the next instrument to be passed through the working channel 4. This is undesirable to a user, as it can contaminate otherwise clean instruments or can obstruct the viewing element of a scope, since the fluid will be deposited on the lens located on the distal-facing surface of the scope. To reduce or eliminate this problem, the user can activate the transducer 102 on the vibratory trocar device 2. As shown in FIG. 8D, when the vibratory trocar device 2 is vibrated, the fluid 810 will be dislodged from the trocar seal 24 and/or the instrument seal 14. Once dislodged, gravitational forces can cause the fluid 810 to drip or otherwise fall distally away from the seals 14, 24 and back into the body cavity 802.

There are several ways in which the transducer can be activated to vibrate the trocar. For example, a user can manually activate the trocar by depressing a foot pedal that is electrically coupled to the transducer or by pressing a button on a remote control or a switch mounted on the trocar itself. The transducer can also be automatically activated when a sensor detects the presence of fluid on or near one or more seals located within the trocar or when a sensor detects fluid elsewhere within the working channel of the trocar or on instruments disposed therein. A sensor can also automatically activate the transducer when it detects that an instrument is about to be inserted into the trocar or is in the process of being inserted into the trocar.

A user can also vibrate the trocar manually, for example by pressing a separate, hand-held vibrator device against it. For example, a user could manually press a standalone transducer against the outer surface of any trocar to cause it to vibrate and thereby remove fluid deposited in the working channel of the trocar.

When vibrating the trocar, several different techniques may be employed. In particular, various vibration parameters can be altered or adjusted by a user in order to optimize the fluid removal process. For example, where a user finds that the scope or viewing instrument is still being contaminated with fluid despite having activated the transducer to vibrate the trocar, the user can try altering various vibration parameters. The user could adjust the frequency and amplitude of the transducer vibration or could activate the transducer for a longer or shorter duration. Additionally, the transducer can be rapidly activated and deactivated to create a series of bursts of vibration. Where a "burst" technique is used, various duty cycles can be employed and/or each burst can have a different amplitude or frequency of vibration. Alternatively, or in addition, the transducer can be activated continuously while sweeping various vibration parameters from one extreme to another. For example, a user can activate the transducer for a fixed duration, during which time the user can gradually ramp the frequency of vibration from a lower frequency to a higher frequency by adjusting a knob or other control operatively coupled to the transducer.

While the methods discussed above involve vibrating an access device to remove fluid deposited therein during the course of a surgical procedure, that need not always be the case. Rather, the methods disclosed herein for removing fluid from a trocar can be performed any time a cleaning is desired, including before initiating a surgical procedure or after the surgery has been completed, just prior to storing the trocar for future use.

Further, the methods disclosed herein can be applied in fields beyond the medical industry. In fact, any application where instruments are passed through an access device can benefit from such methods. In the plumbing industry for example, viewing devices can be passed through an access device for the purpose of viewing the interior of a drain or other pipe to locate blockages or deterioration. Similarly, in the course of repairing or inspecting engines or other complex machines, a viewing device can be passed through an access device to provide visibility into the interior of the machine without completely disassembling it. It is understood that in procedures like these, the methods disclosed herein for removing fluid from an access device can be readily applied.

The devices disclosed herein can be designed to be disposed of after a single use, or can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used tool is obtained and if necessary cleaned. The tool can then be sterilized. In one sterilization technique, the tool is placed in a closed and sealed container, such as a plastic or TYVEK bag. The container and tool are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that the device is sterilized. This can be done by any number of ways known to those skilled in the art including beta or gamma radiation, ethylene oxide, or steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for removing fluid from a trocar, comprising:
   positioning a trocar to extend into a body cavity;
   inserting an instrument through the trocar;
   removing the instrument from the trocar; and
   after removing the instrument from the trocar, activating a vibrator coupled to the trocar to vibrate the trocar and dislodge fluid deposited in the trocar.

2. The method of claim 1, wherein the vibrator comprises an ultrasonic transducer.

3. The method of claim 2, wherein the transducer is activated by a remote control.

4. The method of claim 1, wherein the fluid is deposited on at least one seal disposed within the trocar.

5. The method of claim 1, wherein vibrating the trocar causes the dislodged fluid to pass into a cannula of the trocar.

6. The method of claim 1, further comprising passing a second instrument through the trocar and vibrating the trocar while the second instrument is passed therethrough.

7. The method of claim 1, wherein the vibrator is selectively activated according to an output of a sensor that detects the presence of an instrument in the trocar.

8. The method of claim 1, wherein a sensor detects the presence of fluid at a location within the trocar and an indicator is selectively activated according to an output of the sensor.

9. The method of claim 8, wherein the vibrator is selectively activated according to the output of the sensor.

10. A method for removing fluid from a trocar, comprising:
    activating a transducer coupled to a trocar while the trocar is inserted into a body cavity to vibrate at least one seal disposed within the trocar and thereby remove fluid deposited on the at least one seal by an instrument passed therethrough;
    wherein the transducer is activated after the instrument is removed from the trocar.

11. The method of claim 10, wherein vibration causes the fluid to pass from the at least one seal into a cannula of the trocar.

12. The method of claim 10, wherein the transducer is activated while an instrument is passed through the trocar.

13. The method of claim 10, wherein a sensor detects the presence of an instrument in the trocar and the transducer is selectively activated according to an output of the sensor.

14. The method of claim 10, wherein a sensor detects the presence of fluid at a location within the trocar and an indicator is selectively activated according to an output of the sensor.

15. A method for removing fluid from a trocar, comprising:
    inserting the trocar through tissue to form a working channel extending through the trocar into a body cavity;
    passing an endoscope through the trocar;
    removing the endoscope from the trocar; and
    after removing the endoscope from the trocar, activating a vibrator coupled to the trocar to vibrate the trocar and remove fluid deposited within the trocar by the endoscope.

16. The method of claim 15, wherein the trocar is vibrated ultrasonically.

17. The method of claim 15, wherein the trocar is vibrated mechanically.

18. The method of claim 15, wherein at least one seal disposed within the trocar is vibrated to remove fluid from the at least one seal.

19. The method of claim 15, wherein the vibrator is selectively activated by at least one sensor disposed within the trocar.

20. The method of claim 19, wherein the at least one sensor senses when the endoscope is disposed within the trocar.

* * * * *